USOO5634925A

United States Patent [19]
Urbanski

[11] Patent Number: 5,634,925
[45] Date of Patent: Jun. 3, 1997

[54] APPARATUS AND METHOD FOR SPINAL FIXATION SYSTEM

[75] Inventor: Mark G. Urbanski, San Diego, Calif.

[73] Assignee: Alphatec Manufacturing, Inc., Palm Desert, Calif.

[21] Appl. No.: 429,198

[22] Filed: Apr. 26, 1995

Related U.S. Application Data

[63] Continuation of Ser. No. 342,803, Nov. 21, 1994, abandoned, which is a continuation-in-part of Ser. No. 20,288, Feb. 19, 1993, abandoned.

[51] Int. Cl.$^6$ .................................................. A61B 17/70
[52] U.S. Cl. .............................................. 606/61; 606/73
[58] Field of Search ........................... 606/61, 60, 72, 606/73, 65, 59, 54, 86, 104; 623/17

[56] References Cited

U.S. PATENT DOCUMENTS

| | | |
|---|---|---|
| 4,662,365 | 5/1987 | Gotzen et al. . |
| 4,790,297 | 12/1988 | Luque . |
| 4,913,134 | 4/1990 | Luque . |
| 4,946,458 | 8/1990 | Harms et al. . |
| 4,987,892 | 1/1991 | Krag et al. ............... 606/61 |
| 5,002,542 | 3/1991 | Frigg . |
| 5,047,029 | 9/1991 | Aebi et al. . |
| 5,084,049 | 1/1992 | Asher et al. . |
| 5,092,893 | 3/1992 | Smith .................. 623/17 |
| 5,108,395 | 4/1992 | Laurain . |
| 5,127,912 | 7/1992 | Ray et al. . |
| 5,261,907 | 11/1993 | Vignaud et al. . |
| 5,261,909 | 11/1993 | Sutterlin et al. ........... 606/61 |
| 5,282,801 | 2/1994 | Sherman ................. 606/61 |
| 5,334,203 | 8/1994 | Wagner . |
| 5,487,743 | 1/1996 | Laurain et al. ............ 606/61 |

FOREIGN PATENT DOCUMENTS

| | | |
|---|---|---|
| 3219575 | 5/1982 | Germany . |
| 780652 | 8/1957 | United Kingdom . |
| 8200084 | 1/1982 | United Kingdom . |

OTHER PUBLICATIONS

"Metallurgical Observation of Biomaterials," Compte. Pierre, *Contemporary Biomaterials*, Boretos ed. Noyes Publication. Park Ridge, New Jersey, 1984, pp. 66–91.

"TSRH Spinal System Design Rationale"; pp. 1–11; Danek Group, Inc., 1992 Memphis, Tennessee, Author unknown.

Excerpts from *TSRH Crosslink*™, Surgical Technique Manual; pp. 1–2, 4–8; Danek Medical, Inc., Memphis, Tennessee, Author & Date unknown.

Moss; Excerpts from *Titanium–Mesh–Cylinder*: West Germany, Harms et al., Date unknown.

Moss; Excerpts from *Bone screw with adjustable head*: West Germany, Harms et al., Date unknown.

Excerpts from the *TSRH Spinal Implant System*: pp. 1–14, 16, Date & Author unknown.

Excerpts from *Modular Segmental Spinal–Instrumentation*: West Germany, Date & Author unknown.

AcroMed: Excerpts from *Isola® Spinal System*: 1991; Cleveland, Ohio, USA Author unknown.

"Spinal Stability and Instability: Definitions, Classification, and General Principles of Management", *The Unstable Spine*, by J. Frymoyer, et al., pp. 1–10, 1986.

Excerpts from *Materials Used in Spine Stabilization*, Malinin, et al., pp. 30–32, Date unknown.

"Current Concepts of Internal Fixation", *The Unstable Spine*, by A. Kahn, III, pp. 45–83 1986.

(List continued on next page.)

*Primary Examiner*—Guy V. Tucker
*Attorney, Agent, or Firm*—Knobbe, Martens, Olson & Bear, LLP

[57] ABSTRACT

A vertically adjustable, self-centering spine screw including a bone screw with a beveled head. A series of lateral grooves are disposed on the bone screw head that mesh with similar grooves on an adapter. The second side of the adapter has radial splines that mesh with similar radial grooves on a spacer. This configuration gives the surgeon a self-centering bone screw with adjustment in both the lateral and angular directions.

10 Claims, 3 Drawing Sheets

OTHER PUBLICATIONS

"Surgical Stabilization in Cervical Spine Trauma", *The Spinal Cord Injured Patient: Comprehensive Management*, by D.A. Capen, M.D. 1991.

"Anatomic and Technical Considerations of Pedical Screw Fixation", *Clinical Orthopaedics and Related Research*, by J.N. Weinstein, D.D., et al., pp. 34–46 (Nov. 1992).

"The Use of Intrapedicular Fixation Systems in the Treatment of Thoracolumbar and Lumbosacral Fractures" *Orthopedics*, by M. Zindrick, et al, pp. 337–341 (Mar. 1992).

"A Biomechanical Analysis of Zielke, Kaneda, and Cotrel–Dubousset Instrumentations in Thoracolumbar Scoliosis" *Spine*, by Y. Shono, et al., pp. 1305–1311 (Nov. 1991).

"Experimental Evaluation of Seven Different Spinal Fracture Internal Fixation Devices Using Nonfailure Stability Testing" *Spine*, by R.W. Gaines, Jr., et al., pp. 902–909 (Aug. 1991).

"Triangulation of Pedicular Instrumentation", *Spine*, by C.M. Ruland, et al., pp. S270–S276 (Jun. 1991).

"The Role of Transpedicular Fixation Systems for Stabilization of the Lumbar Spine", *Orthopedic Clinics of North America*, by M.R. Zindrick, pp. 333–334 (Apr. 1991).

"A pedicle screw bridging device for posterior segmental fixation of the spine: preliminary mechanical testing results", *Journal of Biomedical Engineering*, by A.T. Rahmatalla, et al., pp. 97–102 (Mar. 1991).

"Long–Term Lumbar Facet Joint Changes in Spinal Fracture Patients Treated with Harrington Rods", *Spine*, by V.O. Gardner, et al., pp. 479–484 Jun. 1990.

"Anterior Kostiuk–Harrington Distraction Systems for the Treatment of Kyphotic Deformities", *Spine*, by J. P. Kostiuk, pp. 169–180 Mar. 1990.

"Biomechanical Analysis of Pedicle Screw Instrumentation Systems in a Corpectomy Model", *Spine*, by R. Ashman, et al., pp. 1398–1405 Dec. 1989.

"Biomechanical Analysis of Posterior Instrumentation Systems After Decompressive Laminectomy", *Journal of Bone and Joint Surgery*, K. R. Gurr pp. 680–691 Jun. 1988.

"The Role of Harrington Instrumentation and Posterior Spine Fusion in the Management of Adolescent Idiopathic Scoliosis", *Orthopedic Clinics of North America*, by T.S. Renshaw, pp. 257–267 (Apr. 1988).

APPARATUS AND METHOD FOR SPINAL FIXATION SYSTEM

This application is a continuation of U.S. application Ser. No. 08/342,803, filed Nov. 21, 1994, now abandoned, which is a continuation-in-part of U.S. application Ser. No. 08/020,288, filed Feb. 19, 1993, now abandoned.

FIELD OF TECHNOLOGY

This invention relates to prosthetic devices used in spinal fixation systems, such as those used with degenerative, trauma, and deformity conditions. Specifically, this invention relates to bone screw systems for mounting spinal fixation systems to the spine.

BACKGROUND

A wide variety of spinal fixation systems exist. Some systems and their components will be discussed below, and are well known to those skilled in the art of orthopedics. These various systems are meant to help safely secure and stabilize the spine to correct deformities. In addition, spinal implant systems can aid in a healing process from trauma, or assist in degenerative conditions. These types of implants are designed to resist post operative fatigue and failure until bone fusion occurs.

The forces applied to the functional spinal unit include compression, tension, torsion, and shear. The motion associated with a spine is complex since rotations occur in three dimensions. In addition, the spine is a major mechanism for supporting the human upper body. For these reasons, it is important for a spinal fixation unit to provide a high degree of strength and stability.

Bone screws are normally used to attach the spinal fixation apparatus to the spine. Different types of bone screws exist and are used at various points on the spine. Pedicle screws are typically used with instrumentation systems such as a Dynamic Transverse Traction (DTT) unit, the Steffee-VSP system (AcroMed Corporation), or the Isola Instrumentation (AcroMed Corporation, Cleveland, Ohio). Harrington devised the first universally accepted method of internal fixation for the treatment of spinal deformity.

Another spinal fixation system is the TSRH (Texas Scottish Rites Hospital) Spinal System, by Danek Medical, Inc. This system provides temporary stabilization until a solid spinal fusion develops. The TSRH system is used for such conditions as idiopathic scoliosis, neuromuscular scoliosis with associated paralysis or spasticity, spinal fractures, and neoplastic disease. Deficient posterior elements resulting from laminectomy or spina bifida might also call for use of bone screws.

Pedicle screws, hooks, eyebolt assemblies, hex nuts, transverse rods, and cross-links are used in the TSRH system. In the TSRH system, pedicle screws with a "Y" shaped head are fitted into a patient and then fixed to a stabilizing rod that is positioned parallel to the spine. The "Y" shaped head of current TSRH pedicle screws have a mounting grove that helps fix the pedicle screw perpendicular to the stabilization rod. Art eyebolt system holds the pedicle screw head against the retaining rod.

Unfortunately, this system requires the surgeon to forcibly bend the retaining rod to conform to the lordotic (concave) or kyphotic (convex) curves in the surgical area. It is important to avoid excessive bending and rebending of these rods because fatigue resistance decreases as bending increases, leading to a more likely rod failure. Further, the method of bending the rod to fit precisely against the inserted pedicle screws is time consuming and difficult for the surgeon. Eyebolts can also score these rods, leading to earlier rod failure.

Some components have been used between the rod and the bone screw to provide for angular rotation of a pedicle or bone screw. For example, one component of the Danek TSRH system is a washer having radial splines placed between the bone screw and the retaining rod. Radial splines on the bone screw head mesh with the washer and provide a rotational adjustment for the bone screw. Thus, this system prevents the surgeon from having to bend the retaining rod to accommodate a bone screw that is not positioned exactly perpendicular to the rod. However, the surgeon must still bend the rod in the vertical position because the radial splines of the washer and the radial grooves in the bone screw head will not mesh if they are positioned at different vertical heights.

Thus, the surgeon is still required to spend time bending the rod in the vertical direction to overcome this limitation. Further, the surgeon is normally working in a very confined area, and previous spinal fixation systems do not provide a way for easily guiding the bone screw into proper alignment with the rod. Thus, a need exists for a more versatile spinal fixation system.

SUMMARY OF THE INVENTION

The above problems, and others, are overcome by the apparatus and method of this invention in which a spinal fixation system is used for providing stability to bones, such as those found in the spinal column, after degeneration, trauma, or when deformity exists. Additionally, application of the present invention may be found in the larger human bones of the arm or leg, specifically, bones such as the humerus, ulna, radius, or tibia. The system of the present invention includes a washer with a radially channeled surface and a self-centering lateral adapter to overcome limitations in the field.

The total number of components for this system are numerous. The components of each spinal system are a bone screw with a self-centering head, washer with radial channels, an adapter with radial channels on one side and self-centering lateral grooves on the other, a rod, and an eyebolt assembly. In the preferred embodiment all the components are made of a metallic composition, most preferably titanium.

One possible, and preferred construct, has eyebolt assemblies connected to one or more bone screws. Then the rods fit through the eyebolts. The eyebolt assembly for the bone screw would use both the angular rotation spacer and the self-centering height adjustment spacer.

The bone screw, which is height or generally vertically adjustable, has several novel features. One end is an elongated u-shaped yoke. One surface Of the yoke is beveled and serrated with straight or parallel teeth-like grooves. These grooves are oriented across the surface of the yoke, not vertically along the sides of the yoke. The beveled face of the yoke is designed to fit into the height self-centering adapter. The other surface of the yoke is flat or flush.

The self-centering adapter has one side that is slanted outward at an angle designed to match that of the self-centering bone screw. This side of the spacer is serrated with straight or parallel teeth like grooves. These grooves are designed to mesh with the grooves on the bone screw. A novel feature of the adapter is that when inter-connecting with the bone screw, the two angular sections will force the bone screw and the spacer to center on each other, thereby easing the alignment of the bone screw and spacer during spinal surgery.

The rod is typically and preferably used in essentially parallel pairs. The rods are generally flexible and malleable to allow bending to match the curves of the vertebral body. And these rods are oriented generally parallel to the spinal column. The eyebolt assembly generally has the washer next to the eyebolt, then the adapter is on top of the washer, followed by the bone screw and the hex nut. Advantages of the present invention includes provide a self-centering function to allow the surgeon ease in setting the bone screw to the rod and a height-adjustment feature to decrease the amount the surgeon must bend the rods.

These and other aspects of the apparatus and method of the skeletal fixation system of the present invention are set forth more completely in the accompanying figures and the following description.

DETAILED DESCRIPTION OF THE PREFERRED EMBODIMENTS

The present invention is a spinal implant system having a self-centering bone screw. The advantages of this system include the ability to mount the bone screw to the rod without forcing the surgeon to bend the rod during surgery. As will be described in more detail below, the spinal implant system of the present invention allows secure attachment of the bone screw to the rod in various angular and vertical positions.

Figure 1:
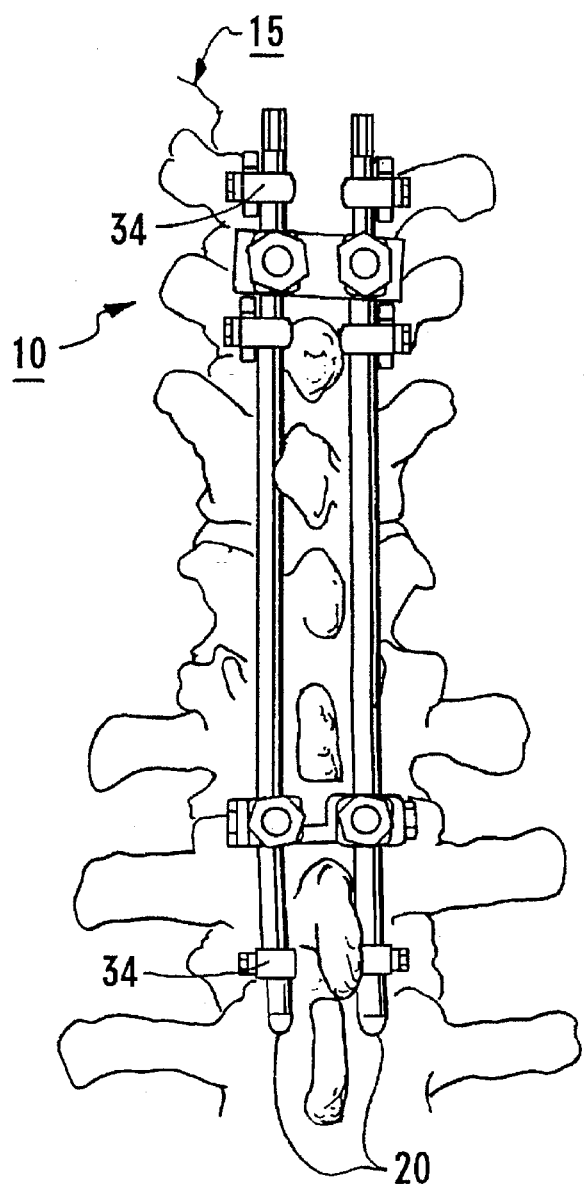
FIG. 1 is a plan view of a preferred embodiment of the spinal fixation system apparatus in place on a skeletal spinal column.

Referring initially to FIG. 1, there is seen a plan view of the spinal fixation apparatus 10 in place on an isolated skeletal spinal column 15. This spinal column 15 is shown in stabilized position. A pair of stabilizing rods 20 are positioned parallel to the direction of the spine. As can be seen, the rods 20 straighten and support the spinal column 15. A number of eyebolts 34 are arranged along each rod 20 to hold various fixation devices. As is known in the art, these fixation devices include pedicle screws, bone screws, hooks and the like.

Figure 2:
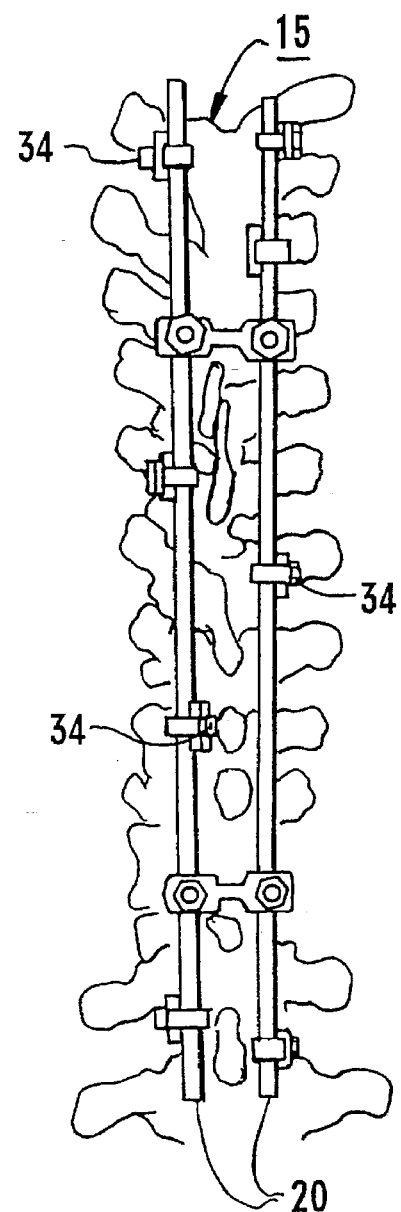
FIG. 2 is a second plan view of another preferred embodiment of the spinal fixation system in place on a skeletal spinal column.

FIG. 2 is a plan view of the spinal fixation apparatus 10 mounted to a deformed spine. As indicated, the rods 20 stabilize and straighten the deformed spine. Eyebolts 34 are placed along the length of the rod 20. Each eyebolt mounts a different fixation device to the rod 20.

Figure 3:
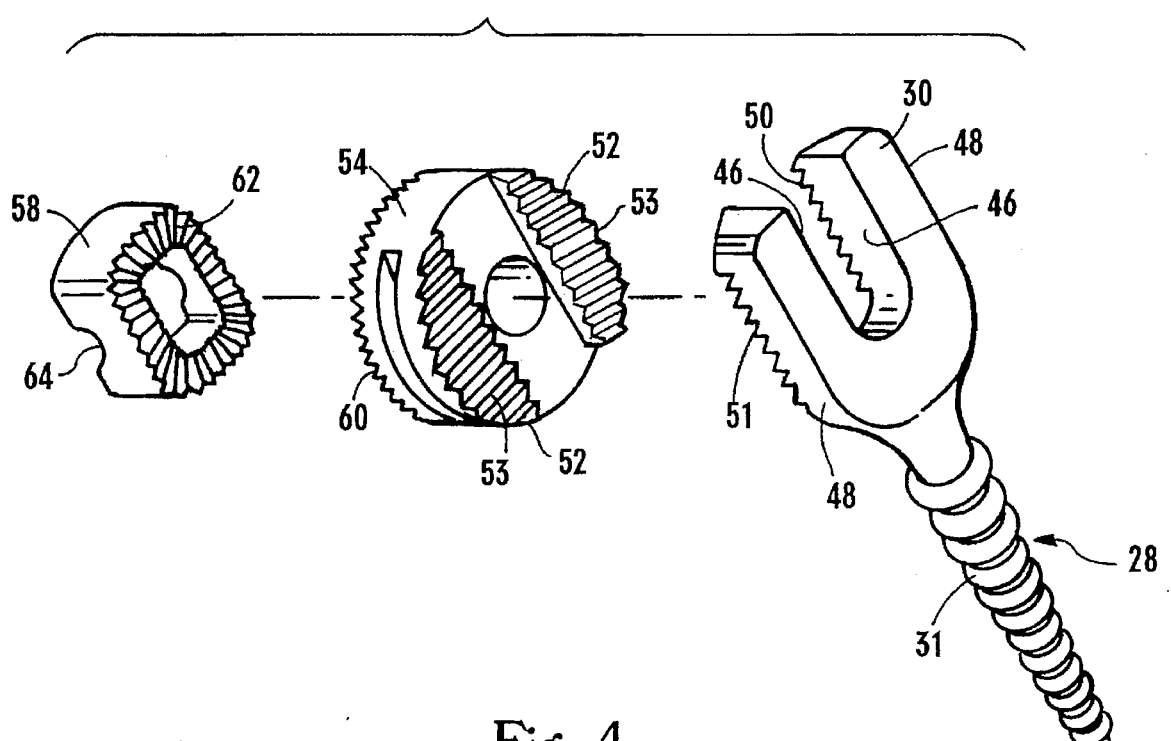
FIG. 3 is a detail exploded perspective view of the adjustable spine bone screw device showing the assembly relationship of the spacers and bone screw of the present invention.
Figure 4:
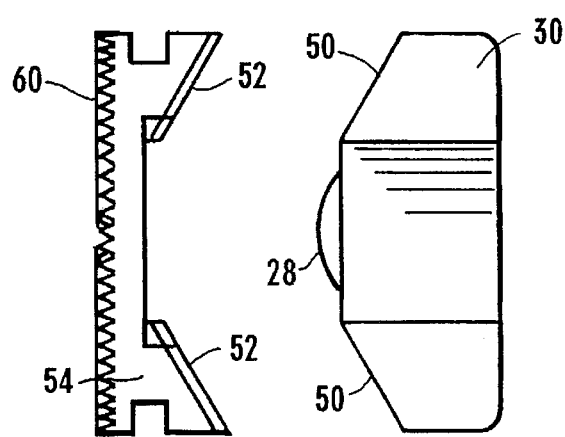
FIG. 4 is a top plan view of the adjustable spine bone screw device showing the self-centering feature of the present invention.

In particular, one preferred fixation device is shown in FIG. 3. FIG. 3 shows a detailed view of a self-centering bone screw 28. As can be seen, the bone screw 28 has a "Y" shaped yoke 30 at the top and a threaded screw portion 31 at the bottom. An inner face 50 of the yoke 30 is beveled so that the yoke 30 is thicker in the center 46 than outer edges or sides 48. In addition, the inner face 50 has lateral grooves 51 that run across the yoke 30. These lateral grooves 51 are designed to mesh with a set of opposing lateral channels 53 on the outer surface of adapter 54. The inner face 50 of the bone screw yoke 30 provides a system for self-centering the bone screw 28 against the adapter As can be appreciated upon review of FIGS. 3 and 4, the lateral channels 53 of the outer surface 52 on the adapter 54 meshes with the lateral grooves 51 of the bone screw beveled face 50. The matching outer surface 52 and inner face 50 provide for the self-centering feature of the bone screw 28. FIG. 4 presents the details of the outer surface 52 of the adapter 54 and the inner face 50 of the bone screw 28. In particular, FIG. 4 reveals that, upon tightening of the bone screw 28 to the adapter 54 (as demonstrated in FIG. 5 by inserting an eyebolt 34 with a threaded stem 35 through the rotation spacer 58, adapter 54 and yoke 30 of the bone screw 28 and then tightening a hex nut 40 on the threaded stem), if the inner face 50 of the bone screw 28 is not centered with respect to the matching outer surface 52 of the adapter 54, the design of the angular surfaces 50 and 52 will force the bone screw yoke 30 to the center of the adapter 54, providing a self-centering effect. This feature allows the surgeon to ensure a proper alignment of the bone screw 28 and adapter 54 during surgical procedures.

Further examination of the lateral grooves 51 in FIG. 3 reveals that the yoke 30 can be mounted to the adapter 54 in various vertical heights. As can be appreciated, the lateral grooves 51 of the yoke 30 will mesh with matching lateral channels 53 on the outer surface 52 of the adapter 54 so that the relative heights between the bone screw 28 and the adapter 54 may be varied while still obtaining a secure attachment between the bone screw 28 and adapter 54. Thus, the bone screw system of the present invention provides a stable vertical height adjustment for the bone screw.

FIG. 3 also shows radial grooves 60 on adapter 54. The radial grooves 60 are on the face opposing the lateral channels 53 and are configured to mesh with matching radial channels 62 on an angular rotation spacer 58. The matching radial grooves 60 on the adapter 54 radial channels 62 on the angular rotation spacer 58 provide the bone screw 28 with an angular adjustment capability. By virtue of the lateral grooves 51 and lateral channels 53, and the radial grooves 60 and radial channels 62, the bone screw 28 can be fixedly adjusted in both the vertical and angular directions. This provides a distinct advantage over prior systems. The inner face 50 of the bone screw 28 provides further advantages by helping guide the yoke 30 against the adapter 54 during surgery.

A grooved inner surface 64 of angular rotation spacer 58 is used to keep the angular rotation spacer 58 from rotating about the rod 20 when installed. To accomplish this, the radius of the grooved inner surface 64 of the angular rotation spacer 58 approximately matches the radius of rod 20.

Figure 5:
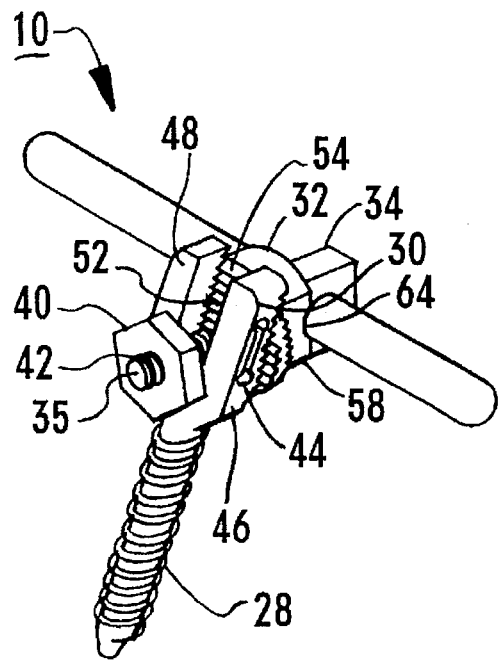
FIG. 5 is a perspective view of one preferred embodiment of the present invention.

A complete spinal fixation system is illustrated in FIG. 5. The self-centering bone screw 28 is shown mounted to an adapter 54 which is in meshed attachment to the angular rotation spacer 58. The eyebolt 34 has a threaded stem 35 which runs through the angular rotation spacer 58, adapter 54, and bone screw 28. A grooved inner surface 64 on the angular rotation spacer 58 surrounds a portion of the rod 20, and thereby keeps the angular rotation spacer 58 from rotating about the eyebolt 34. A hex nut 40 is used to tighten the bone screw 28 against the adapter 54. As can be appreciated, upon review of FIGS. 5 and 6A, the bone screw 28 can be adjusted in the vertical direction by selecting a different position for the yoke 30 in relation to the adapter 54. The lateral grooves 50 on the yoke 30 of the bone screw 28 and the adapter 54 mesh to fixedly attach the bone screw 28 to the adapter 54 in various vertical positions.

Figure 6A:
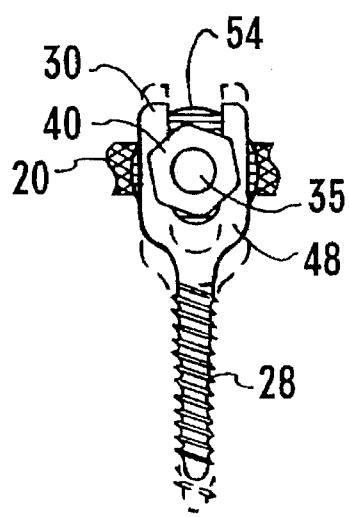
FIG. 6a is an elevation view of an adjustable spine bone screw device showing the height adjustment feature of the present invention.
Figure 6B:
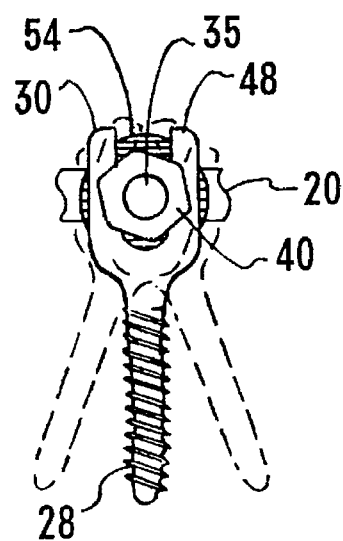
FIG. 6b is an elevation view of the adjustable spine bone screw device showing the rotational adjustment feature of the present invention.

It can also be appreciated upon review of FIGS. 5 and 6B that the bone screw 28 can be angularly adjusted with respect to the rod 20 by virtue of the radial grooves 60 on the adapter 54 and the radial channels 62 on the angular rotation spacer 58. Thus, prior to tightening the hex nut 40 against the bone screw 28, a surgeon can adjust the angle of the bone screw 28 to keep the rod 20 parallel to the spine.

Referring next to FIG. 6a, there is seen an elevation view of bone screw 28 showing the height adjustment feature. As was described above, the relative heights between the bone screw 28 and the adapter 54 may be varied while still obtaining a secure attachment between the bone screw 28 and adapter 54. This height adjustment feature allows the surgeon to place the eyebolt in the spine without having to bend the spinal rods. This makes the insertion of the screws easier and does not place any undue metal fatigue due to bending on the spinal rods. One possible height adjustment variation of yoke 30 is shown. In phantom are shown two other variations in height adjustment. Eyebolt hex nut 40 is tightened in one of these positions or others, depending on the location of the construct within the pedicle region of the vertebral body of a patient.

Referring now to FIG. 6b, there is seen a detail schematic elevation view of the bone screw 28 showing the angular rotation adjustment feature. As was described above, the bone screw 28 may be attached to the adapter 54 at a variety of angles. This feature allows the bone screw to be inserted perpendicular to the spinal bone without movement of the spinal rods 20. This bone screw 28 is interchangeable with a variety of standard lengths with associated threads per inch. Shown more clearly in this view are some typical angular orientations of bone screw 28.

All components in the various constructs are preferably Ti6Al4V and are overall surface treated to prevent galling and fretting. Galling is scuffing or denting of metal due to friction between metallic parts. Fretting is a breaking away of metallic pieces due to friction between parts. This surface treatment is done in an interstitial chemical process where each part is dipped into a chemical bath, thereby covering the part with a protective coating.

It can be seen that the present invention provides a novel apparatus and method which provides a breakthrough in applying the concepts of skeletal fixation systems.

Because the bone screw head and adapter have matching beveled faces, during engagement the bone screw will center itself while attaching to the adapter. The advantage of this configuration is that the surgeon doesn't have to exactly center the bone screw against the adapter during surgery. Spine surgery of this type is performed in an area that is very cramped. Thus, the system of the present invention allows the surgeon to place the bone screw head against the adapter, and let the bone screw center itself as it is tightened in place.

During surgery, bone screws are first attached to different positions along the pateint's spine. After placing the bone screws into the spine, an assembly containing the retaining rod, adapter, spacer and eyebolt are positioned near the bone screw. The lateral grooves on the first face of said bone screw head are then put in contact with matching lateral grooves on the first side the adapter. As discussed above, the meshing of these lateral grooves allows the bone screw to attach at various vertical heights to the retaining rod. The radial splines on the adapter and spacer allow for the bone screw to mount in varying angular positions with respect to the retaining rod. After placing the bone screw in contact with the adapter, a nut is tightened over the eyebolt threaded stem. Tightening of the nut causes said bone screw to center itself with respect to the adapter.

The foregoing description of the present invention is explanatory thereof and various changes in the size, or shape, as well as on the details of the illustrated construction may be made, within the scope of appended claims without departing from the spirit of the invention.

What is claimed is:

1. A bone screw assembly for a spinal fixation apparatus comprising:
   a bone screw having a "U" shaped beveled head and a threaded tail, wherein the beveled head of said bone screw has lateral grooves on one face;
   an adapter having lateral channels on a first face and radial grooves on a second face, wherein said first face is beveled to mesh with the beveled head of said bone screw; and
   a spacer having radial grooves on a first side, wherein said radial grooves mesh with the radial grooves on said second face of said adapter.

2. The assembly according to claim 1 wherein said assembly is made from titanium.

3. The assembly according to claim 1 wherein said adapter has a central hole to allow passage of an eyebolt threaded stem.

4. The spinal fixation system according to claim 1 wherein said adapter has a central hole to allow passage of an eyebolt threaded stem.

5. A method of installing a spinal fixation device into a patient comprising:
   attaching a bone screw having a beveled head to the spine of said patient, said beveled head also having lateral grooves on a first face;
   mounting said bone screw to a retaining rod, wherein said mounting includes the steps of
   a) contacting the lateral grooves on the first face of said bone screw head with matching lateral grooves on a first side an of adapter, and
   b) contacting radial splines on a second side of said adapter to matching splines on a spacer; and
   connecting said beveled bone screw, adapter and spacer to said retaining rod with an eyebolt and nut wherein tightening said nut causes said bone screw to center itself with respect to said adapter.

6. The method of claim 5 wherein said bone screw has a 'U' shaped head.

7. The method of claim 5 wherein said bone screw, adapter, rod and spacer are made of titanium.

8. The method of claim 5 wherein the height of said rod is adjusted with respect to said bone screw by meshing the lateral grooves on said adapter to a different set of lateral grooves on the bone screw head.

9. A spinal fixation system including a plurality of rods, hooks and eyebolts comprising:
   a bone screw having a "U" shaped beveled head and a threaded tail, wherein the beveled head of said bone screw has lateral grooves on one face;

an adapter having lateral channels on a first face and radial grooves on a second face, wherein said first face is beveled to mesh with the beveled head of said bone screw; and a spacer having radial grooves on a first side, wherein said radial grooves mesh with the radial grooves on said second face of said adapter and wherein said spacer is mounted to said rod by an eyebolt.

10. The spinal fixation system according to claim 9 wherein said system is made from titanium.

* * * * *